(12) United States Patent
Ichikawa et al.

(10) Patent No.: US 7,686,795 B2
(45) Date of Patent: Mar. 30, 2010

(54) PULL-ON DIAPER

(75) Inventors: Makoto Ichikawa, Kagawa-ken (JP);
Naoto Ohashi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/673,171

(22) Filed: Feb. 9, 2007

(65) Prior Publication Data
US 2007/0233033 A1 Oct. 4, 2007

(30) Foreign Application Priority Data
Mar. 28, 2006 (JP) .............................. 2006-089188

(51) Int. Cl.
*A61F 13/15* (2006.01)
(52) U.S. Cl. ...................... 604/387; 604/386; 604/391; 604/389; 604/385.03
(58) Field of Classification Search ............ 604/385.01, 604/385.03, 391, 389, 386, 387
See application file for complete search history.

(56) References Cited

U.S. PATENT DOCUMENTS

| | | | |
|---|---|---|---|
| 5,074,854 A | 12/1991 | Davis | |
| 5,370,634 A * | 12/1994 | Ando et al. ............ | 604/385.21 |
| 5,531,732 A | 7/1996 | Wood | |
| 5,624,428 A | 4/1997 | Sauer | |
| 5,662,638 A | 9/1997 | Johnson et al. | |
| 6,210,388 B1 | 4/2001 | Widlund et al. | |
| 6,287,287 B1 * | 9/2001 | Elsberg ................. | 604/385.03 |
| 6,579,275 B1 | 6/2003 | Pozniak et al. | |
| 6,972,012 B1 | 12/2005 | Pozniak et al. | |
| 2006/0089616 A1 | 4/2006 | Belau et al. | |

FOREIGN PATENT DOCUMENTS

| | | |
|---|---|---|
| JP | 05-317356 A | 12/1993 |
| JP | 06-031725 U | 4/1994 |
| JP | 2003-339772 | 12/2003 |
| WO | 2004/047704 A1 | 6/2004 |
| WO | 2006134895 A1 | 12/2006 |

* cited by examiner

*Primary Examiner*—Jacqueline F. Stephens
(74) *Attorney, Agent, or Firm*—Lowe Hauptman Ham & Berner, LLP

(57) ABSTRACT

A pull-on diaper includes a front waist region and a rear waist region joined together along joints defined by transversely opposite edges of these waist regions so as to form a waist-hole and a pair of leg-holes. The joints are adapted to be ruptured for disposal of the diaper which has been used. The front waist region and the rear waist region are joined together along the joints by means of joining members and each of the joining members is provided with a gripper formed integrally with this joining member and rupture guides extending from the gripper toward the waist-hole and the associated one of the leg-holes.

18 Claims, 4 Drawing Sheets

PULL-ON DIAPER

BACKGROUND OF THE INVENTION

The present invention relates generally to a pull-on diaper and particularly to a disposable pull-on diaper having transversely opposite side edges adapted to be broken away after used for disposal.

Disposable pull-on diapers having transversely opposite side edges adapted to be broken away after used for disposal is well known. For example, Japanese Unexamined Patent Application Publication No. 2003-339772, para. 0013-0014, FIG. 3 (hereinafter referred to as "Reference"), discloses a disposable pull-on diaper comprising an absorbent component and an outer cover made of a nonwoven fabric or the like adapted to be folded back on itself in a longitudinal direction to define two halves which are then bonded together along transversely opposite edges of these two halves by a means such as heat sealing so as to form side seal patterns. This pull-on diaper is characterized in that each of the side seal patterns comprises a plurality of elements continuously or intermittently arranged in a vertical direction in which the two halves of the outer cover will be torn off from each other, these elements presenting a locus such that each of these elements has a width as measured in a transverse direction which is orthogonal to a direction extending from a start point of tearing off to an end-point of tearing off is gradually enlarged from the start point of tearing off to the maximum width whereupon this width is gradually reduced until the end-point of tearing off is reached.

According to the disclosure of Reference, the seal pattern is easily ruptured in the direction of tearing off and not easily ruptured in the direction orthogonal to this direction of tearing off. However, to tear off the transversely opposite edges of this pull-on diaper, one side of the waist-hole must be held by both hands and twisted to tear off this side edge and then the other side edge must be torn off in the same manner. Such operation takes a lot of trouble particularly when the transversely opposite edges of the pull-on diaper worn by an infant are ruptured and taken off from the wearer's body.

SUMMARY OF THE INVENTION

To solve the problem as has been described above, it is an object of the present invention to provide a pull-on diaper improved so that each of the transversely opposite edges of the diaper can be ruptured with one hand after the diaper has been used.

According to the present invention, there is provided a diaper comprising a front waist region and a rear waist region joined together along joints defined by transversely opposite edges of these two waist regions so as to form a waist-hole and a pair of leg-holes, the joints being adapted to be ruptured for disposal of the diaper which has been used.

The diaper according to the present invention further comprises the front waist region and the rear waist region being joined together along the joints by means of joining members, and each of the joining members being provided with a gripper formed integrally with the joining member and rupture guides extending from the gripper toward the waist-hole and the associated one of the leg-holes, respectively.

The present invention includes preferred embodiments as follow:

The embodiment wherein the gripper is a finger-grip formed by making a cut in a part of the joining member and the rupture guides extend from upper and lower roots of the finger-grip, respectively;

The embodiment wherein the rupture guides respectively comprise a plurality of incisions arranged to extend stepwise from the gripper toward the waist-hole and associated one of the leg-holes, respectively, at given intervals;

The embodiment wherein the rupture guides respectively comprise a plurality of incisions arranged to extend stepwise from the gripper toward the waist-hole and associated one of the leg-holes, respectively, at given intervals and each pair of the adjacent incisions partially overlap each other as viewed in a direction orthogonal to a longitudinal direction of the incisions;

The embodiment wherein the joining member is made of a fibrous nonwoven fabric comprising fibers oriented in on direction, a length of the incision being shorter than a length of the fibers, a distance between each pair of the adjacent incisions being the same as or shorter than the length of the incisions, and the longitudinal direction of the incisions is orthogonal to the one direction in which the fibers of the fibrous nonwoven fabric are oriented; and The embodiment wherein the gripper is located between the waist-hole and the associated one of the leg-holes.

In the pull-on diaper according to the present invention, the front waist region and the rear waist region are joined together along the joints by means of the joining members each being provided with the gripper formed integrally with this joining member and the rupture guides extending from the gripper toward the waist-hole and the associated one of the leg-holes, respectively. Such construction advantageously permits the gripper to be held and to be pulled with one hand of a caretaker such as a mother so that the joining member may be ruptured along the rupture guides extending from the gripper of the joining member to the waist-hole and the associated one of the leg-holes, respectively. The front waist region and the rear waist region of the pull-on diaper are torn off from each other and the pull-on diaper can be taken off from the wearer's body for disposal. The front waist region and the rear waist region are joined together by means of the joining member provided with the rupture guides in this manner, resulting in the pull-on diaper allowing each of the transversely opposite edges to be ruptured with one hand instead of holding and rupturing each of the transversely opposite sides of the waist-hole with both hands as the conventional pull-on diaper has been the case.

In the embodiment wherein the rupture guides comprise a plurality of the incisions arranged from the gripper toward the waist-hole and the associated one of the leg-holes at predetermined intervals, the joining member can be easily ruptured along a plurality of the incisions.

In the embodiment wherein the rupture guides respectively comprise a plurality of incisions arranged to extend stepwise from the gripper toward the waist-hole and associated one of the leg-holes, respectively, at given intervals and each pair of the adjacent incisions partially overlap each other as viewed in a direction orthogonal to a longitudinal direction of the incisions, a force converges from the gripper on the immediately adjacent incisions to rupture the portion between the gripper and the immediately adjacent incisions. In the same manner, the force is transmitted from the incisions thus ruptured to the immediately adjacent incisions successively and thus the joining member can be easily ruptured along a plurality of the incisions.

Generally, the long fiber nonwoven fabric characterized by a high fiber orientation in a given direction has the highest strength in this fiber oriented direction. In the embodiment wherein the joining member is made of a fibrous nonwoven fabric comprising fibers oriented in on direction and a length of the incision is shorter than a length of the fibers; wherein a distance between each pair of the adjacent the incisions is the same as or shorter than the length of the incisions; and wherein the longitudinal direction of the incisions is orthogonal to the one direction in which the fibers of the fibrous nonwoven fabric are oriented, operation of rupturing can be carried on by means of the incisions in the direction orthogonal to the fiber oriented direction, i.e., in the direction along which rupture is difficult and then operation of rupturing can be carried on in the fiber oriented direction along which rupture is easy. In this way, the joining member can be smoothly ruptured.

The length of the incisions is shorter than the length of the fibers constituting the nonwoven fabric and therefore the fiber length of the nonwoven fabric is adequately maintained to ensure the desired strength of the nonwoven fabric. The distance between each pair of the adjacent incisions is the same as or shorter than the length of the incisions and correspondingly the process of rupturing is facilitated along the fiber oriented direction. Consequently, the joining member is not easily ruptures during use of the diaper but easily ruptured for disposal of the used diaper.

DETAILED DESCRIPTION OF THE PREFERRED EMBODIMENTS

First Embodiment

Figure 1:
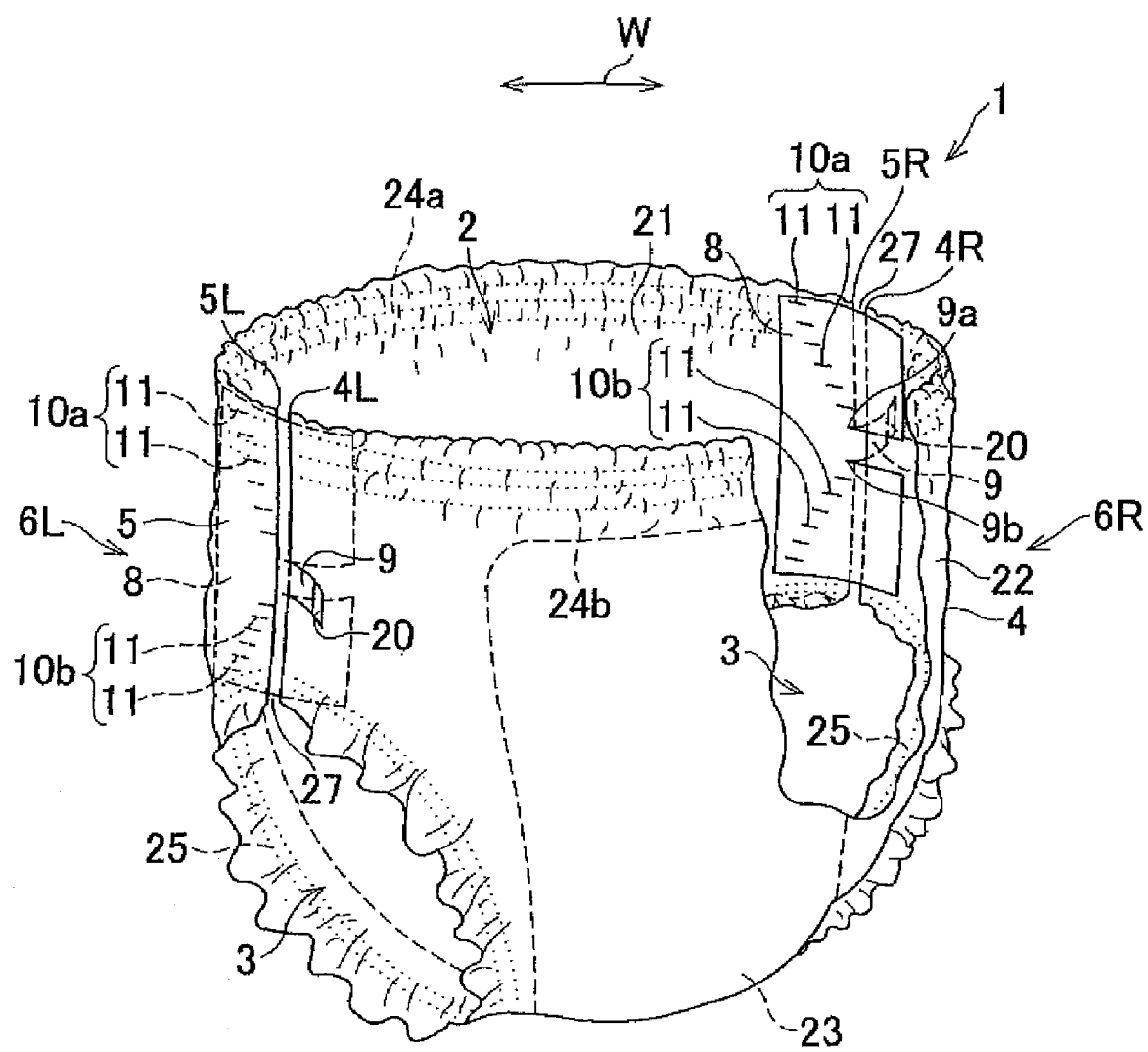
FIG. 1 is a partially cutaway perspective view of a disposable pull-on diaper.

Details of a disposable pull-on diaper according to the present invention will be more fully described in reference with the accompanying drawings. FIG. 1 is a partially cutaway perspective view of a disposable pull-on diaper 1 (hereinafter simply referred to as "diaper 1") according to the present invention. The diaper 1 comprises a composite panel primarily including a liquid-pervious inner sheet 21 adapted to come in contact with the wearer's skin, a liquid-impervious outer sheet 22 opposed to the inner sheet 21, and a liquid-absorbent panel 23 sandwiched between these two sheets 21, 22. The diaper 1 is generally divided into a front waist region 4 and a rear waist region 5.

The diaper 1 shown in FIG. 1 has transversely opposite edges bowing inward about a border between the front and rear waist regions 4, 5, i.e., in a crotch region so that the transversely opposite edges become concave inward in the crotch region (not shown). Accordingly, the diaper 1 has an hourglass-like planar shape when it is developed and flattened. Such hourglass-shaped composite panel is folded along an intermediate region (i.e., the crotch region) so as to put the front waist region 4 and the rear waist region 5 flat together. The transversely opposite edges of the front waist region 4 are bonded to the associated edges of the rear waist region 5 by means of joining members 8 which are interposed between these associated side edges. Thus the diaper is formed with a waist-hole 2 and a pair of leg-holes 3, 3. The waist-hole 2 is provided along front and rear halves of its periphery with waist-surrounding elastic members 24a, 24b, respectively, attached in a stretched state thereto and the leg-holes 3, 3 are provided along respective peripheries thereof with leg-surrounding elastic members 25, 25, respectively, attached in a stretched state thereto. The liquid-absorbent panel 23 is interposed between the inner sheet 21 and the outer sheet 22 so that the liquid-absorbent panel 23 may match a crotch region of the wearer.

The front waist region 4 and the rear waist region 5 are bonded to each other in respective joint regions 6L, 6R extending from the waist-hole 2 to the respective leg-holes 3 along the transversely opposite edges of the respective waist regions 4, 5 by means of the respective joining members 8, 8. Each of the joining members comprises a finger-grip 9, a first rupture guide 10a extending from the finger-grip 9 toward the waist-hole 2 and a second rupture guide 10b extending from the finger-grip 9 toward the associated one of the leg-holes 3.

In the joint regions 6L, 6R for the transversely opposite edges of the diaper 1, the edges 4L, 5L as well as the edges 4R, 5R of the front and rear waist regions 4, 5 are opposed to each other and able to come in contact with each other but not jointed to each other. In other words, each pair of the edges 4L, 5L or 4R, 5R can be put apart from each other with the hands of a caretaker to form a gap 27. The finger-grip 9 is provided to face this gap 27 so that the finger-grip 9 can be pulled out from the diaper 1 as seen in FIG. 1. It should be understood here that the waist-surrounding elastic members 24a, 24b are separated from each other along these gaps 27 and the leg-surrounding elastic members 25, 25 are also interrupted by the gaps 27, respectively.

The joining members 8, 8 serving to join the front and rear waist regions 4, 5 are provided along the transversely opposite edges so as to cover a dimension of the respective edges extending from the vicinity of the waist-hole 2 to the vicinities of the respective leg-holes 3. That is, each of the joining members 8, 8 has a longitudinal dimension slightly shorter than the dimension extending from the waist-hole 2 to the respective leg-holes 3. The joining member 8 is preferably formed from a breathable spun-bond nonwoven fabric of polypropylene long fibers exhibiting the strength of 40 to 55 N/25 mm in the fiber oriented direction and the strength of 28 to 30 N/25 mm in the direction orthogonal to the fiber oriented direction. It is also possible without departing from the scope of the invention to form the joining member 8 from the fibrous nonwoven fabric made of short or long fibers of the other material such as rayon, nylon or polyester subjected to the process of well known art, for example, air-laying, spun-bonding or melt-blowing processes.

Figure 2:
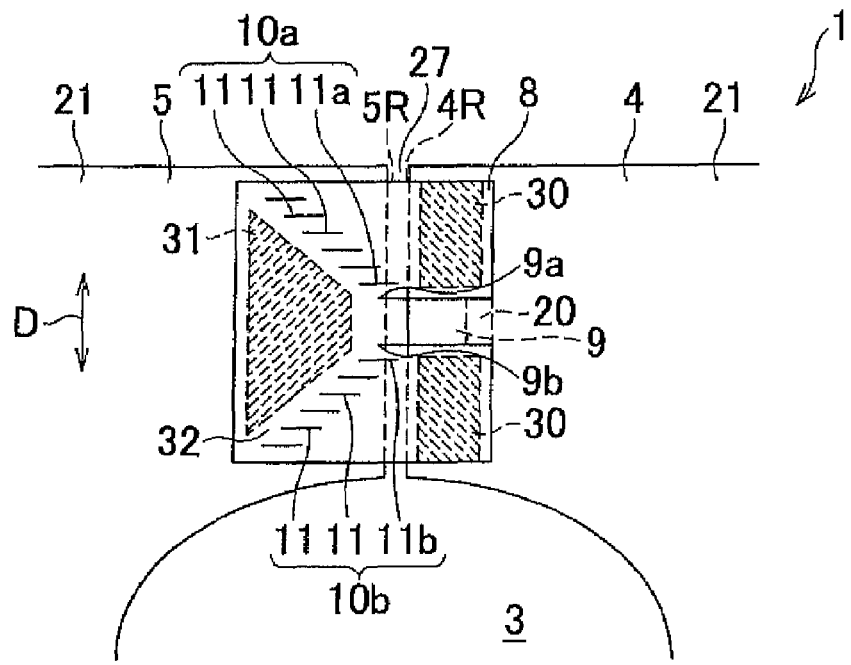
FIG. 2 is a diagram schematically illustrating a bonding member including a finger-grip according to a first embodiment of the present invention.

The joining member 8 is required to meet the contradictory properties that the member 8 should not be easily ruptured during use of the diaper 1 but should be easily ruptured for disposal of the used diaper 1. Generally, the long fiber nonwoven fabric characterized by a high fiber orientation in a given direction has a strength higher than that of the short fiber nonwoven fabric but can be easily ruptured under a force exerted thereon in the fiber oriented direction. Accordingly, such long fiber nonwoven fabric is able to meet the contradictory requirements as have been described above and suitable as the material for the joining member 8. The fiber oriented direction of the joining member 8 indicated by a double-headed arrow D in FIG. 2 is orthogonal to a waist-circumferential direction W extending in parallel to a transverse direction of the diaper 1. In other words, the fiber oriented direction corresponds to a longitudinal direction of the diaper 1.

The finger-grip 9 is formed integrally with the joining member 8 in a manner that the finger-grip 9 lies between the waist-hole 2 and the associated leg-hole 3 after the joining member 8 has been attached to the diaper 1. Under a force exerted thereon, the finger-grip 9 serves as a start point of rupture and thereby facilitates the joining member 8 to be ruptured. According to the first embodiment, there is no anxiety that the finger-grip 9 might unnecessarily function as the start point of rupture and consequently cause the joining member 8 to be unintentionally ruptured even when a force tending to expand a diameter of the waist-hole 2 or the associated leg-hole 3 due to movement of the wearer is exerted on the joining member 8 because the finger-grip 9 lies between the waist-hole 2 and the associated leg-hole 3.

The finger-grip 9 is formed integrally with the joining member 8 by providing the joining member 8 with a pair of cut lines extending in parallel to each other from a central zone to one side edge thereof. The joining member 8 is attached to the diaper 1 so that these two cut lines may extend in parallel to the waist-circumferential direction W. The finger-grip 9 includes a reinforcing member 20 bonded to a distal end thereof, which has a rigidity sufficiently higher than that of the joining member 8 to ensure that the finger-grip 9 can be easily held with one hand of a caretaker and the finger-grip 9 is reliably prevented from being torn off when the caretaker intends to rupture the joining member 8. Stock materials for such reinforcing member 20 may be selected from the group including nonwoven fabrics having a basis weight higher than that of the joining member 8 or plastic films.

A first rupture guide 10a extends from an upper root of the finger-grip 9 toward the waist-hole 2 and a second rupture guide 10b extends from a lower root 9b of the finger-grip 9 toward the associated leg-hole 3. These first and second rupture guides 10a, 10b respectively comprise a plurality of incisions 11 arranged stepwise at given intervals. According to this embodiment, the incisions 11 are provided in the form of slits each having its longitudinal direction corresponding to the waist-circumferential direction W, i.e., being orthogonal to the fiber oriented direction of the nonwoven fabric constituting the joining member 8. As will be described later, the joining member 8 is ruptured from the start point defined by the finger-grip 9 along the first and second rupture guides 10a, 10b respectively defined by the incisions 11, 11, . . . .

The length of the respective incisions 11 as well as the interval at which each pair of the adjacent incisions 11 is spaced from each other may be selected so as to satisfy the requirement that the joining member 8 should not be ruptured during use of the diaper 1 but easily ruptured for disposal of the used diaper 1. To satisfy this requirement, the length of the incision 11 is preferably shorter than the fiber length in the fibrous nonwoven fabric and the interval at which each pair of the adjacent incisions 11 is preferably shorter than the length of the incision 11. More specifically, the length of the incision 11 may be selected to be shorter than the fiber length to assure the strength of the nonwoven fabric sufficiently high to prevent the joining member 8 from being ruptured during use of the diaper 1. The interval at which each pair of the adjacent incisions 11 is spaced from each other may be selected to be the same as or shorter than the length of the incision 11 to converge the rupturing force for the joining member 8 on a limited area between each pair of the adjacent incisions 11 so that the joining member 8 may be easily ruptured. According to this embodiment, the length of the incision 11 is in a range of 4 to 8 mm, and the interval between each pair of the adjacent incisions is in a range of 1 to 5 mm.

Figure 3:
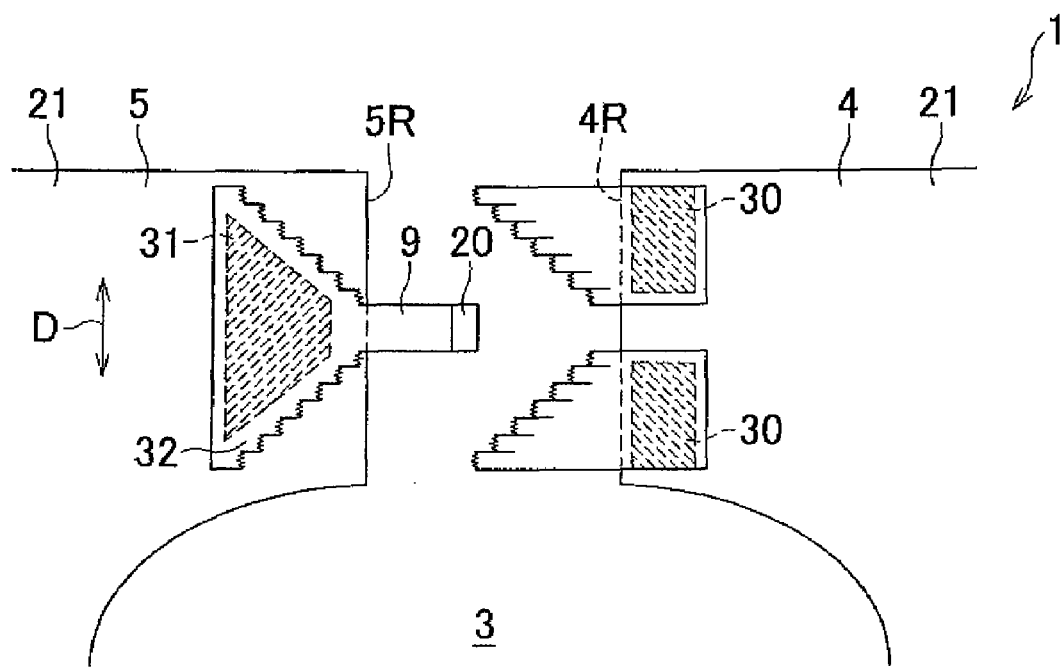
FIG. 3 is a diagram schematically illustrating the bonding member including a finger-grip wherein the bonding member has been broken apart.

Now an attachment feature and rupture process of the joining member 8 will be described with reference to FIGS. 2 and 3. FIG. 2 is a schematic diagram illustrating the right side joining member 8 and the vicinity thereof shown in FIG. 1 as viewed from the inner side of the diaper 1 wherein the gap 27 is slightly opened. FIG. 3 schematically illustrates the same joining member 8 after has been ruptured.

The joining member 8 is bonded to a first attachment area 30 defined on the front waist region 4 and to a second attachment area 31 defined on the rear waist region 5. The first attachment area 30 is spaced apart from the right side edge 4R of the front waist region 4 by a predetermined distance and so as to avoid any interference with the finger-grip 9. The second attachment area 31 is defined by an area 32 surrounded by a plurality of the incisions 11 and this area 32 is spaced apart from the right side edge 5R of the rear waist region 5 by a predetermined distance. The gap 27 is left between the front waist region 4 and the rear waist region 5 so that the upper and lower roots 9a, 9b of the finger-grip 9 are located to face the gap 27. Bonding of the joining member 8 to the front waist region 4 and the rear waist region 5 may be carried out using the method of well known art such as pressure-sensitive adhesive, heat embossing or heat sealing.

The first and second rupture guides 10a, 10b respectively comprise a plurality of incisions 11 arranged stepwise extend from the upper and lower roots 9a, 9b of the finger-grip 9 toward the waist-hole 3 and the associated leg-hole 3. Each of the incisions 11 has its longitudinal direction extending in parallel to the transverse direction of the diaper 1 and as viewed in the direction orthogonal to the longitudinal direction, each pair of the adjacent incisions 11 partially overlaps each other. A pair of the incisions 11 lying nearest to the upper and lower roots 9a, 9b of the finger-grip 9 is provided to intersect with a line connecting the upper and lower roots 9a, 9b of the finger-grip 9.

As has previously described above, the longitudinal direction of the incision 11 is parallel to the transverse direction of the diaper 1, i.e., parallel to the waist-circumferential direction W. With such directional relationship, even when a force tending to expand the waist-hole 2 is exerted on the diaper 1, the incisions 11 are not deformed and the fibrous nonwoven fabric well stands against the force. Consequently, there is no possibility that the joining member 8 might be unintentionally ruptured during use of the diaper 1.

To rupture the joining member 8 for the used diaper 1, the finger-grip 9 is raised with one hand of the caretaker from the gap 27 and pulled outward from the diaper 1 (pulled perpendicularly rearward with respect to the plane defined by FIG. 2). Thereupon, a force is transmitted from the upper and lower roots 9a, 9b of the finger-grip 9 to the immediately adjacent incisions 11a, 11b in the longitudinal direction of the diaper 1 until a partial rupture of the joining member 8 occurs from the upper and lower roots 9a, 9b to the immediately adjacent incisions 11a, 11b. Such rupture progresses in the fiber oriented direction of the nonwoven fabric, i.e., in the longitudinal direction of the diaper 1 in which the strength is relatively low. In this manner, rupture progresses from the incisions 11a, 11b successively toward the outermost incisions 11, 11.

More specifically, the second attachment area 31 in which the joining member 8 is attached to the rear waist region 5 is defined within a region 32 surrounded by a plurality of the incisions 11, so the region 32 surrounded by the incisions 11 of the joining member 8 is moved together with the rear waist region 5 outward from the diaper 1 as the finger-grip 9 is pulled outward from the diaper 1. However, the remaining portion of the joining member 8 is unable to follow the region 32 as well as the rear waist region 5 and progressively spaced apart from the rear waist region 5. Consequently, rupture progresses as the portions defined between respective pairs of the adjacent incisions 11, 11 are successively ruptured.

After the joining member 8 has been completely ruptured, the region 32 surrounded by a plurality of the incisions 11 of the joining member 8 remains together with the finger-grip 9 on the rear waist region 5 while the other region of the joining member 8 remains on the front waist region 4, as shown in FIG. 3. The rupturing process progresses along the fiber oriented direction of the nonwoven fabric from the rear end of one incision to the intermediate point of the next incision. After the process of rupturing has been completed, the first and second rupture guides 10a, 10b present a shape as shown in FIG. 3.

According to this embodiment, as has been described above, the component fibers of the nonwoven fabric are oriented in the longitudinal direction of the diaper 1 while the longitudinal direction of the respective incisions 11 corresponds to the waist-circumferential direction W and each pair of the adjacent incisions 11 partially overlap each other as viewed in a direction orthogonal to a longitudinal direction of the incisions 11. Such construction is effective to eliminate a fear that the joining member 8 might be unintentionally ruptured during use of the diaper 1 and allows the joining member 8 to be easily ruptured with one hand of the caretaker along a plurality of the incisions 11 and the fiber oriented direction of the nonwoven fabric.

Second Embodiment

Figure 4:
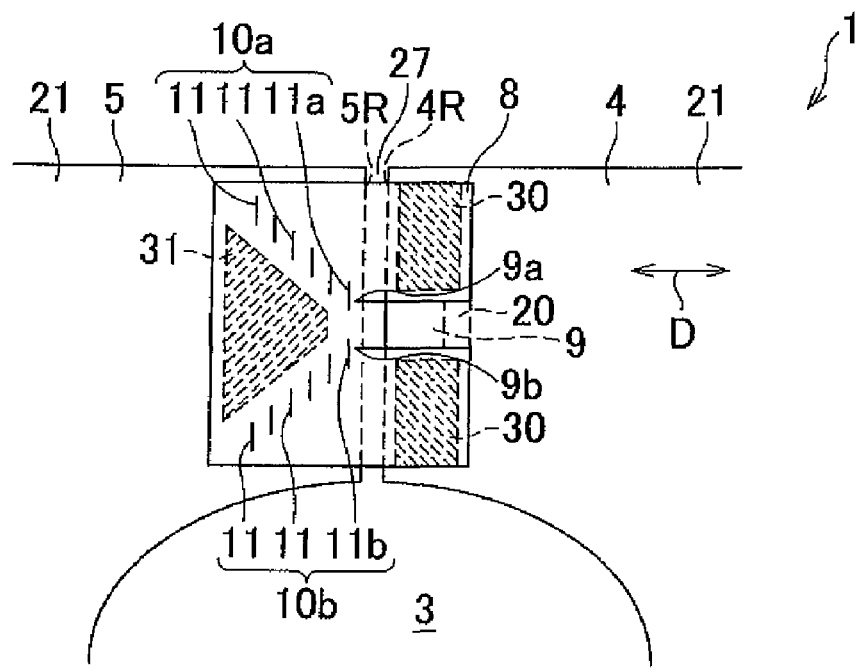
FIG. 4 is a diagram schematically illustrating a bonding member including a finger-grip according to a second embodiment of the present invention.

FIG. 4 is a schematic diagram illustrating the joining member 8 according to a second embodiment of the present invention wherein the longitudinal direction of the incisions 11 is parallel to the longitudinal direction of the diaper 1 while the fiber oriented direction of the nonwoven fabric is parallel to the waist-circumferential direction W of the diaper 1 as indicated by the double-headed arrow D. In this embodiment, the length of the incisions 11 as well as the distance between each pair of the adjacent incisions 11 is dimensioned to be larger than in the first embodiment. The other aspects are similar to the corresponding aspects of the first embodiment and will be described as briefly as possible, if necessary.

The incisions 11 are opened in the waist-circumferential direction W under a force directed to expand the diameter of the waist-hole 2. As a result, a plurality of the incisions 11 as a whole is deformed in an accordion-like shape adapted to absorb the force. The other features including the relatively large distance between each pair of the adjacent incisions 11 and the fiber oriented direction of the nonwoven fabric parallel to the waist-circumferential direction W allow the joining member 8 to resist the force. In this way, there is no anxiety that the joining member 8 might be unintentionally ruptures during use of the diaper 1.

When it is desired to discard the used diaper 1, the finger-grip 9 may be pulled in the waist-circumferential direction W by a force higher than a force exerted to the joining member 8 when the diaper 1 is put on the wearer's body. Thus the joining member 8 is ruptured along a plurality of the incisions 11 and the fiber oriented direction in the same manner as in the first embodiment. Specifically, in the initiation step of rupturing, the joining member 8 is ruptured from the upper and lower roots 9a, 9b of the finger-grip 9 toward the immediately adjacent incisions 11a, 11b, then toward the further adjacent incisions 11, 11 and such rupturing process progresses until the front waist region 4 and the rear waist region 5 are disconnected from each other.

Third Embodiment

Figure 5:
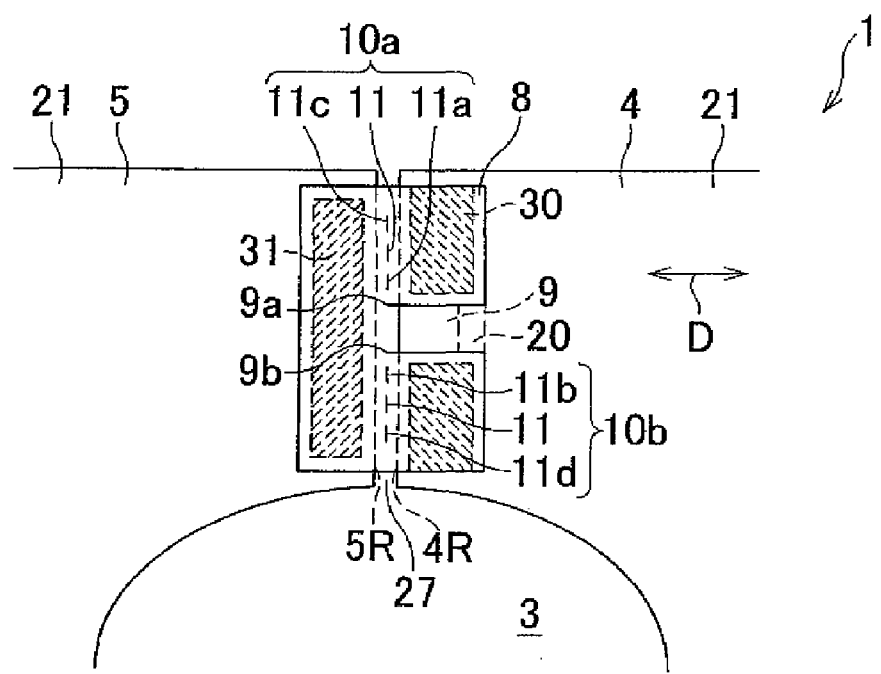
FIG. 5 is a diagram schematically illustrating a bonding member including a finger-grip according to a third embodiment of the present invention.

FIG. 5 is a schematic diagram illustrating a third embodiment of the present invention wherein each of the incisions 11 extends in the longitudinal direction of the diaper 1 and these incisions 11 are arranged on a straight line extending in parallel to the longitudinal direction of the diaper 1. Such construction contributes to saving of an amount used to form the joining member 8. The fiber oriented direction of the nonwoven fabric is parallel to the waist-circumferential direction W of the diaper 1 as indicated by the double-headed arrow D. In this embodiment, each of the incisions 11 has a length of 5 mm and a distance between each pair of the adjacent incisions 11 is in a range of 2 to 7 mm. A distance from the upper and lower roots 9a, 9b to the immediately adjacent incisions 11a, 11b is in a range of 3 to 7 mm. In the vicinity of the waist-hole 2 as well as in the vicinity of the leg-holes 3, none of the incisions are provided. In this embodiment, a distance from the waist-hole 2 and the leg-holes 3 to the incisions which are nearest to these waist- and leg-holes 2, 3 is in a range of 28 to 32 mm. The other aspects of this embodiment are similar to the relevant aspects in the first embodiment and will be described as briefly as possible, if necessary.

A force exerted on the diaper put on the wearer's body and tending to expand the diameter of the waist-hole 2 causes the incisions 11 to be opened in the waist-circumferential direction W but fibers of the nonwoven fabric oriented in this waist-circumferential direction W adequately resists such force to prevent the joining member 8 from being unintentionally ruptured during use of the diaper 1. In addition, none of the incisions 11 is present in the vicinity of the waist-hole 2 as well as in the vicinity of the leg-holes 3. Therefore, even when a force is exerted on the waist-hole 2 or the leg-holes 3, there is no possibility that the joining member 8 might unintentionally begin to be ruptured from the incisions 11c, 11d as the start points.

When it is desired to discard the used diaper 1, the finger-grip 9 may be pulled in the waist-circumferential direction W by a force higher than a force exerted to the joining member 8 when the diaper 1 is put on the wearer's body to ensure that the force is converged from the upper and lower roots 9a, 9b of the finger-grip 9 to the immediately adjacent incisions 11a, 11b in the longitudinal direction of the diaper 1. Thereby the joining member 8 begins to be ruptured in the direction orthogonal to the fiber oriented direction because the distance from the upper and lower roots 9a, 9b of the finger-grip 9 to the immediately adjacent incisions 11 is relatively short. In the same manner, such rupturing process progresses until the front waist region 4 and the rear waist region 5 are disconnected from each other.

Fourth Embodiment

Figure 6:
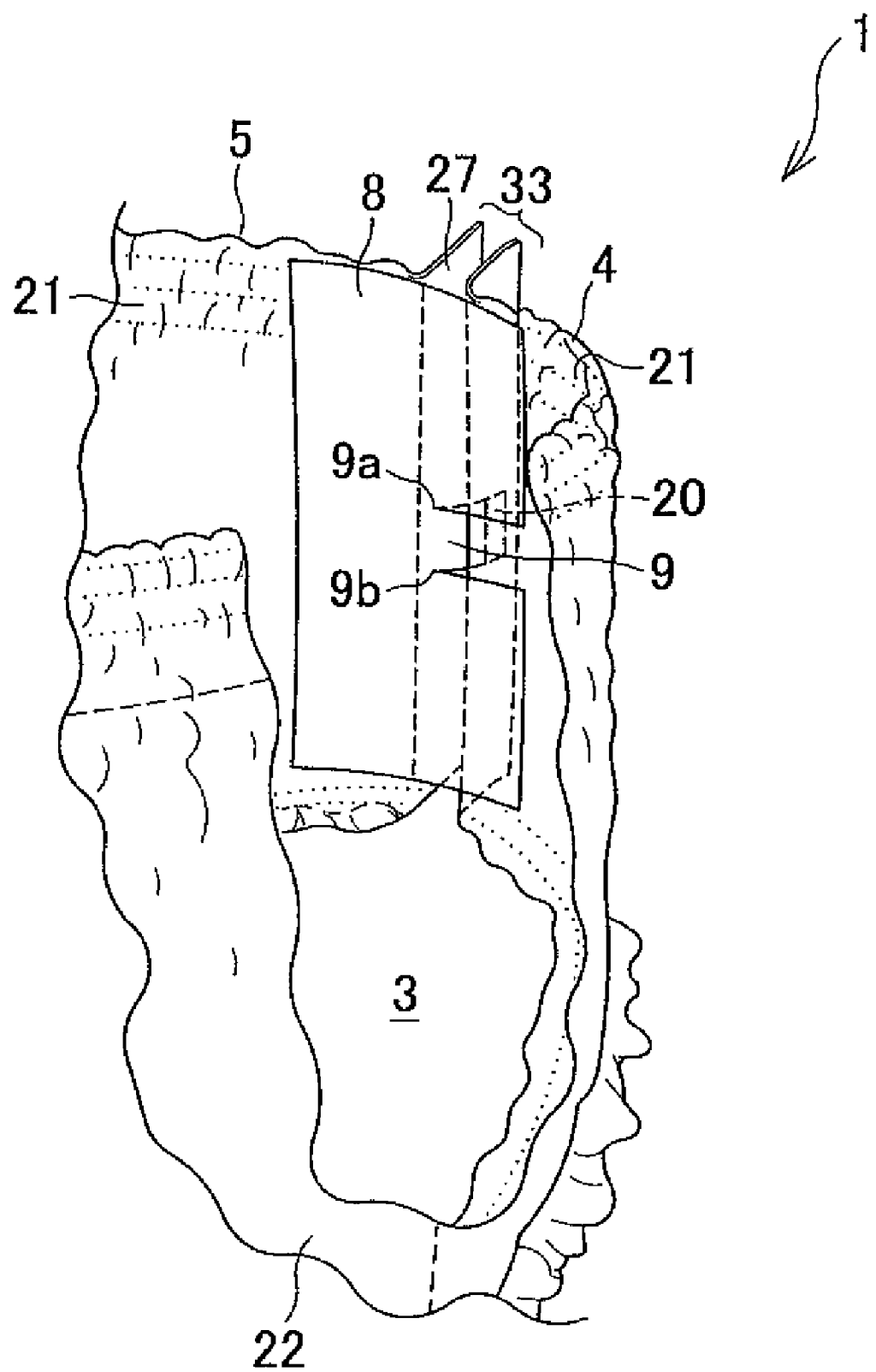
FIG. 6 is a diagram schematically illustrating a bonding member including a finger-grip according to a fourth embodiment of the present invention.

FIG. 6 is a schematic diagram illustrating a construction of the joining member 8, particularly of the finger-grip 9 thereof according to a fourth embodiment of the present invention, wherein only one side edge of the diaper 1 is illustrated in an enlarged scale and the rupture guides 10a, 10b are not illustrated to avoid complexity. In this embodiment, one side edge of the front waist region 4 and the corresponding side edge of the rear waist region 5 are folded back along a line extending between the upper and lower roots 9a, 9b of the finger-grip 9 of the joining member 8 so that these two side edges may form projection 33 with the inner sheet 21 thereof in a face-to-face relationship. With the finger-grip 9 interposed between the projections 33, the front and rear waist regions 4, 5 are joined together by means of the joining member 8 to obtain the finished diaper 1.

Along the respective projections 33, the front waist region 4 and the rear waist region 5 are not joined together and leave the gap 27 therebetween similarly to the first embodiment. The upper and lower roots 9a, 9b of the finger-grip 9 is located on a bottom of the gap 27 and accordingly the finger-grip 9 is interleaved between the projections 33 of the front and rear waist regions 4, 5. With such construction, the finger-grip 9 can be easily found and pulled with one hand of the caretaker to rupture the joining member 8.

While the present invention has been described on the basis of the first, second, third and fourth embodiments, these particular embodiments do not limit the invention but may be variously varied and modified without departing from the scope of the invention. For example, the incisions 11 have been described to be provided in the form of slits, it is possible to provide the incisions in the form of rectangular or oval incisions. It is also possible to dimension a distance between the paired incisions 11, 11 immediately adjacent the upper and lower roots 9a, 9b of the finger-grip 9 to be narrower than a distance between the paired incisions 11, 11 adjacent the waist-hole 2 or the associated leg-hole 3 in order to facilitate the joining member 8 to be ruptured. Furthermore, it is also possible to form the finger-grip 9 by making a squared U-shaped cut in the joining member 8.

The entire discloses of Japanese Patent application No. 2006-89188 filed on Mar. 28, 2006 including specification, drawings and abstract are herein incorporated by reference in its entirety.

What is claimed is:

1. A pull-on diaper, comprising a front waist region and a rear waist region joined together, by means of joining sheets, along transversely opposite side edges of said waist regions so as to form a waist-hole and a pair of leg-holes;
   each of said joining sheets being permanently bonded to both the front and rear waist regions along the respective side edges of said waist regions; and
   each of said joining sheets being provided with a finger-grip formed integrally with the joining sheet and rupture guides extending from said finger-grip toward said waist-hole and the associated one of said leg-holes, respectively, wherein said rupture guides define weakened zones along which rupture of said joining sheet is to be effected when said finger-grip is pulled, thereby facilitating separation of the respective side edges of said waist regions and removal of the diaper from a wearer after use;
   wherein said joining sheets are not bonded to the front and rear waist regions at the rupture guides;
   said front and rear waist regions do not overlap each other in a circumferential direction of said waist-hole, are not directly attached to each other, and are completely spaced from each other in the circumferential direction of said waist-hole by two gaps each between one of the side edges of said front waist region and a respective one of the side edges of said rear waist region; and
   each of the joining sheets bridges one of said two gaps between said front and rear waist regions in the circumferential direction of said waist-hole.

2. The pull-on diaper defined by claim 1, wherein
   said finger-grip is partially cut from said joining sheet and has a root portion where said finger-grip remains attached to said joining sheet; and
   said rupture guides extend upward and downward from said root portion of said finger-grip towards said waist-hole and the associated leg-hole, respectively.

3. The pull-on diaper defined by claim 2, wherein
   the finger-grip is partially cut from the joining sheet by cutting lines elongated in a circumferential direction of said waist-hole; and
   the weakened zones extend essentially an entire length of the respective joining sheet in a longitudinal direction of the diaper between said waist-hole and the respective leg-hole, whereby rupture occurs over essentially the entire length of the respective joining sheet when said finger-grip is pulled in the circumferential direction of said waist-hole to completely disconnect the respective side edges of the waist regions from each other in said circumferential direction.

4. The pull-on diaper defined by claim 2, wherein
   each said joining sheet is permanently, directly bonded to the respective side edge of one of the front and rear waist regions at first and second bonding sites which are positioned between the finger-grip and the waist-hole and the associated leg-hole, respectively; and
   each said joining sheet is permanently, directly bonded to the respective side edge of the other one of the front and rear waist regions at a third bonding site which is separated, in a circumferential direction of said waist-hole, from the first and second bonding sites by said weakened zones.

5. The pull-on diaper defined by claim 1, wherein said rupture guides respectively comprise a plurality of incisions arranged in ascending and descending stepwise fashion from said finger-grip toward said waist-hole and the associated one of said leg-holes, respectively.

6. The pull-on diaper defined by claim 5, wherein each pair of the adjacent incisions partially overlap each other as viewed in a direction orthogonal to a longitudinal direction of said incisions.

7. The pull-on diaper defined by claim 5, wherein
   said joining sheet is made of a fibrous nonwoven fabric comprising fibers which are oriented orthogonal to a longitudinal direction of said incisions and have a fiber length greater than a length of said incisions; and
   a distance between each pair of the adjacent said incisions is the same as or shorter than said length of said incisions.

8. The pull-on diaper defined by claim 5, wherein
   said incisions are elongated in a circumferential direction of said waist-hole; and
   the fiber are oriented in a longitudinal direction of said diaper between said waist-hole and the associated one of said leg-holes.

9. The pull-on diaper defined by claim 7, wherein
   said incisions are elongated in a longitudinal direction of said diaper between said waist-hole and the associated one of said leg-holes; and
   the fiber are oriented in a circumferential direction of said waist-hole.

10. The pull-on diaper defined by claim 5, wherein said incisions are elongated in a circumferential direction of said waist-hole.

11. The pull-on diaper defined by claim 5, wherein said incisions are elongated in a longitudinal direction of said diaper between said waist-hole and the associated one of said leg-holes.

12. The pull-on diaper defined by claim 5, wherein a distance between each pair of the adjacent incisions in a vicinity of the finger-grip is smaller than in a vicinity of the waist-hole and the associated leg-hole.

13. The pull-on diaper defined by claim 1, wherein said finger-grip is located between said waist-hole and the associated one of said leg-holes.

14. The pull-on diaper defined by claim 1, wherein
said rupture guides respectively comprise a plurality of incisions arranged in a single line along a longitudinal direction of said diaper between said waist-hole and the associated one of said leg-holes.

15. The pull-on diaper defined by claim 14, wherein
said joining sheet is made of a fibrous nonwoven fabric comprising fibers, which are oriented in a circumferential direction of said waist-hole to be orthogonal to said longitudinal direction of said diaper and have a fiber length greater than a length of said incisions.

16. The pull-on diaper defined by claim 1, wherein
each said joining sheet is permanently, directly bonded to the respective side edge of the front waist region at a first bonding site, and to the respective side edge of the rear waist region at a second bonding site which is separated, in a circumferential direction of said waist-hole, from the first bonding site by said weakened zones.

17. The pull-on diaper defined by claim 1, wherein
the finger-grip of each of the joining sheets is disposed in the respective gap between said front and rear waist regions.

18. A pull-on diaper, comprising a front waist region and a rear waist region joined together, by means of joining sheets, along transversely opposite side edges of said waist regions so as to form a waist-hole and a pair of leg-holes;

each of said joining sheets being permanently bonded to both the front and rear waist regions along the respective side edges of said waist regions; and each of said joining sheets being provided with a finger-grip formed integrally with the joining sheet and rupture guides extending from said finger-grip toward said waist-hole and the associated one of said leg-holes, respectively, wherein said rupture guides define weakened zones along which rupture of said joining sheet is to be effected when said finger-grip is pulled, thereby facilitating separation of the respective side edges of said waist regions and removal of the diaper from a wearer after use;

wherein the respective side edges of said front and rear waist regions are spaced from one another, in a circumferential direction of said waist-hole, without being directly attached to one another; and the respective joining sheet bridges a spacing between the respective side edges of said front and rear waist regions;

the respective side edges of said front and rear waist regions are bent outwardly in a radial direction of the waist hole to define a gap therebetween; and said finger-grip is also bent outwardly in the radial direction of the waist hole to be disposed in said gap between the respective side edges of said front and rear waist regions.

* * * * *